US009241772B2

United States Patent
Modrow et al.

(10) Patent No.: US 9,241,772 B2
(45) Date of Patent: Jan. 26, 2016

(54) METHOD FOR PREPARING THE RECONSTRUCTION OF A DAMAGED BONE STRUCTURE

(75) Inventors: Daniel Modrow, Ottobrunn (DE); Jens Witte, Munich (DE)

(73) Assignee: Brainlab AG, Feldkirchen (DE)

( * ) Notice: Subject to any disclaimer, the term of this patent is extended or adjusted under 35 U.S.C. 154(b) by 177 days.

(21) Appl. No.: 14/004,696

(22) PCT Filed: Mar. 17, 2011

(86) PCT No.: PCT/EP2011/054034
§ 371 (c)(1),
(2), (4) Date: Sep. 12, 2013

(87) PCT Pub. No.: WO2012/123029
PCT Pub. Date: Sep. 20, 2012

(65) Prior Publication Data
US 2014/0005685 A1    Jan. 2, 2014

(51) Int. Cl.
*G06K 9/00* (2006.01)
*A61B 19/00* (2006.01)

(52) U.S. Cl.
CPC ........... *A61B 19/50* (2013.01); *A61B 2019/502* (2013.01); *A61B 2019/508* (2013.01)

(58) Field of Classification Search
None
See application file for complete search history.

(56) References Cited

U.S. PATENT DOCUMENTS

| 2004/0152972 A1 | 8/2004 | Hunter |
| 2008/0319448 A1 | 12/2008 | Lavallee et al. |
| 2009/0226068 A1 | 9/2009 | Fitz et al. |

OTHER PUBLICATIONS

International Search Report for International Application No. PCT/EP2011/054034 dated Jan. 3, 2012.

*Primary Examiner* — Atiba O Fitzpatrick
(74) *Attorney, Agent, or Firm* — Tucker Ellis, LLP

(57) ABSTRACT

A method for preparing the reconstruction of a damaged bone structure using an implant, comprising the following steps which are carried out by a computer (2): a) performing atlas segmentation on a structure dataset which represent the structure to be reconstructed, and determining healthy objects and defective objects within the damaged structure; b) determining a target structure by modelling replacements for the defective objects within the damaged structure; c) selecting an implant on the basis of the target structure, and providing a shape dataset which represents the shape of the implant; d) positioning the selected implant in order to find the optimum implant position; e) determining whether or not the selected implant is suitable, and returning to step c) if the implant is determined to not be suitable; and f) exporting the suitable implant to a medical navigation process.

15 Claims, 2 Drawing Sheets

METHOD FOR PREPARING THE RECONSTRUCTION OF A DAMAGED BONE STRUCTURE

Figure 1:
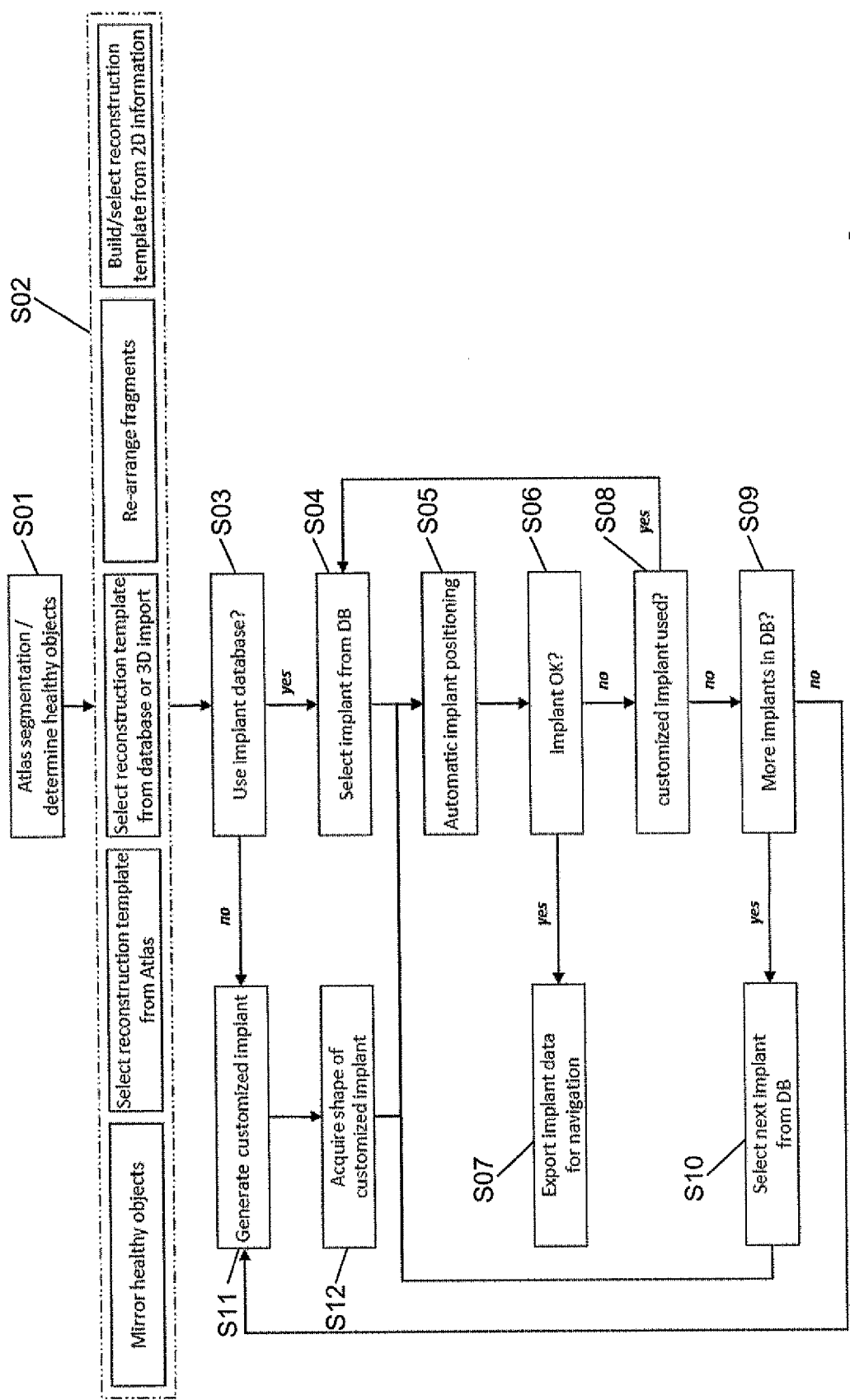

This application is a national phase of International Application No. PCT/EP2011/054034 filed Mar. 17, 2011 and published in the English language.

The present invention relates to a method, a computer program and an apparatus for preparing the reconstruction of a damaged bone structure using an implant.

A common form of damage to bone structures is a fracture. Other kinds of damages might be caused by a tumour or a congenital defect, for example causing a part of the bone structure being missing or removed. A fractured or removed/missing bone structure is usually reconstructed using an implant. The problem to be solved by the present invention is that of improving and simplifying preparation of the reconstruction, in particular finding a suitable implant for the affected bone structure.

This problem is solved by the independent claims. Advantageous embodiments are described in the dependent claims.

The present invention relates to a method for preparing the reconstruction of a damaged bone structure using an implant. The first step of this method involves performing atlas based segmentation on a structure dataset which represents an affected region with the structure to be reconstructed, i.e. the damaged structure, and determining healthy objects and defective objects within the damaged structure. The structure dataset preferably is a diagnostic image of the damaged structure. "Reconstruction" means physically creating a structure which is for example identical or similar to the affected bone structure before it was damaged or which resembles the bone structure without the defect. "Preparing" the reconstruction means that the (theoretical) preconditions for performing the actual reconstruction are established. Preparing the reconstruction in particular comprises finding a suitable implant and/or a suitable position of the implant within the bone structure. An object is the bone structure or preferably a part of the bone structure.

The damaged structure consists of healthy objects and defective (or missing) objects. If the damage is a fracture, then a defective object is typically divided or fractured into a plurality of fragments. Healthy objects within the structure are those which are not defective. The structure dataset preferably comprises two-dimensional or three-dimensional image data of the damaged structure. The structure dataset can for example be generated using x-ray or computer tomography (CT). The structure dataset is preferably provided to a computer which then performs the atlas based segmentation. The objects in the segmented structure dataset are then partitioned into healthy objects and defective objects, either manually by utilising classification data represented by a classification dataset and provided by a surgeon, the classification data indicating healthy or defective objects, or automatically, for example from a mismatch between an object in the matched atlas and the corresponding area in the structure dataset. Another approach is to provide pre-classification data represented by a pre-classification dataset to the segmentation process, wherein the pre-classification data indicates damaged objects. Damaged objects are then excluded from the matching process of the atlas to the structure dataset.

An "atlas" typically consists of a plurality of generic models of objects, wherein the generic models of the objects together form a complex structure. The atlas of a femur, for example, can comprise the head, the neck, the body, the greater trochanter, the lesser trochanter and the lower extremity as objects which make up the complete structure. The atlas of the skull can comprise the frontal bone, mandible, maxilla, sphenoid bone, orbits, zygomatic bones, temporal bones, parietal bones, occipital bone, nasal bone, and so on. One application of such an atlas is in the segmentation of medical images, wherein the atlas is matched to medical image data, and by comparing the image data with the matched atlas, a point (a pixel or voxel) of the image data can be assigned to an object in the matched atlas, thereby segmenting the image data into objects. Preferably, one object in the atlas corresponds to one object within the bone structure. However, one object in the atlas can correspond to a plurality of objects within the patient's bone structure, or a plurality of objects in the atlas can correspond to one object within the patient's bone structure.

The structure data are preferably provided using the DICOM (digital imaging and communications in medicine) standard.

The second step of the method involves determining a target structure by modelling replacements for the defective objects within the damaged structure. This means that the computer generates the target structure in such a way that it exhibits a desired shape. The target structure represents the shape of the bone structure or parts of the bone structure as it/they should look after the reconstruction process. The desired shape is in particular identical or similar to the shape of the (original) bone structure or parts of the (original) bone structure. The target structure is preferably represented by a target structure dataset, such as a digital 3D dataset.

The third step of the method involves selecting an implant and providing a shape dataset which represents the shape of the implant, wherein "selecting" means in particular that the computer automatically picks out one of the available implants. This implant exhibits a shape which is then used in the subsequent method steps. This shape can be known, and can in particular have known dimensions, or can be measured. If the shape is measured, one possible embodiment is that the implant is scanned and the shape dataset is created, for example as a digital file.

In a fourth step, the selected implant is positioned in order to determine an implant position. Preferably, the implant is automatically positioned to find the optimum implant position. The implant position is the position of the implant, as represented by the shape dataset, relative to the healthy objects within the damaged structure, as represented by the structure dataset. The combination of the healthy objects within the damaged structure and the implant therefore represents the theoretical shape of the bone structure after reconstruction. Automatic implant positioning optionally takes into account additional criteria such as prohibited areas into which the implant must not protrude or areas which need to be accessed for surgery. Automatic implant positioning is in particular a step of virtually positioning the implant and is preferably performed on the structure dataset and the shape dataset by the computer.

In a fifth step, a determination is made as to whether or not the selected implant is suitable, and the method returns to the third step if the implant is determined to not be suitable. The determination is preferably made automatically by the computer, for example by comparing the target structure with the positioned shape dataset or a combination of the structure dataset and the positioned shape dataset. The implant is suitable if the shape of the implant matches the shape of the target structure or a part of the target structure to a predetermined level of accuracy. For determining suitability, an appropriate measure of similarity, such as a least squares measure, can be designed and applied. Certain criteria such as the external contours of the implant or the transition of the implant to neighbouring objects can be given an increased significance in evaluating suitability. External contours are those which face the outside of the body and thus have a greater impact on the appearance of the patient than contours which face inwards. The transition to neighbouring objects relates to gaps between the implant and the surrounding objects and in particular to minimising these gaps.

If the implant is considered to be suitable, then it is exported to a medical navigation process in a sixth step of the method. Exporting the implant can for example mean exporting a reference to the implant, the shape dataset representing the shape of the implant, the (optimum) position of the implant or a combination thereof.

A medical navigation process is used to track the relative positions of objects such as medical instruments or body structures such as bones or bone fragments. Such a medical navigation process uses a navigation system (image guided surgery system).

A navigation system, in particular a medical navigation system, is understood to mean a system which can comprise: at least one marker device; a transmitter which emits infrared light, electromagnetic waves and/or radiation and/or ultrasound waves; a receiver which receives infrared light, electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for outputting an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data which have been stored in said memory beforehand.

In one embodiment, the target structure is in particular determined by mirroring healthy objects to replace the corresponding defective object. The healthy objects can be taken from the damaged structure, from a corresponding structure which resembles the damaged structure or from the atlas. If the damaged bone structure is a structure which is basically mirror-symmetric, such as the skull, then a replacement for a defective object within the bone structure can be modelled by a target structure which is equivalent to a mirrored healthy counterpart of the damaged object. If the bone structure itself is not mirror-symmetric, a healthy object within a corresponding structure can be used and in particular mirrored. If, for example, a bone in one hand or foot is damaged, then the corresponding bone in the other hand or foot in each case can be mirrored and thus used as the target structure.

In another embodiment, determining the target structure involves selecting at least parts of the atlas as the target structure. This embodiment utilises the fact that the matched atlas represents the bone structure, including the defective objects in their non-defective condition, to a high level of accuracy. The parts of the atlas corresponding to the defective objects within the bone structure therefore represent the nominal condition of the bone structure and can therefore be used as the target structure.

In another embodiment, determining the target structure involves selecting a template from a database or selecting an imported 3D template as the target structure. The selection is preferably made automatically. The database comprises a set of templates in different shapes and/or sizes. In one implementation, the template which best fills the gap between the healthy objects within the bone structure is chosen. In another implementation, the template which best matches some or all of the fragments of a fractured object within the bone structure is chosen. In yet another implementation, the template which best corresponds to a healthy object within the damaged structure or another structure is chosen.

It is also possible to import a 3D template as a target structure. In this approach, the target structure can be designed in any way. The template can for example be modelled in a computer so as to fit the healthy objects within the damaged bone structure as well as possible.

In another embodiment, determining the target structure involves rearranging fragments of an object of the damaged structure in order to model the target structure. The relative positions of the fragments are for example modified until the fragments represent the non-damaged state of the bone structure.

In another embodiment, determining the target structure involves building the target structure from 2D information. This 2D information can for example be photographs of the patient. Methods for reconstructing the underlying bone structure from photographs of a patient, even if there is tissue and/or skin over the bone, are known in the art. One implementation is to use 2D information of the patient. Another implementation is to use 2D information from another person, such that the appearance of the patient can be changed in the direction of the appearance of another person. The 2D information is optionally used to select a template from the database.

When the target structure, i.e. the desired shape of the bone structure after reconstruction, has been determined, a suitable implant then has to be selected. In one embodiment, selecting the implant means selecting the implant from a database which comprises a set of implants in a variety of shapes and/or sizes. These implants are preferably available as pre-manufactured implants provided by an implant supplier. Using readily available implants allows an immediate surgical reconstruction after the planning process.

In another embodiment, selecting the implant means selecting an implant which is generated as a customised implant. Such a customised implant can be manufactured to perfectly adapt to the desired reconstructed bone structure as well as the surrounding remaining structures. Preferably, the target structure can be exported to a manufacturing process for the customised implant. This means that the customised implant perfectly matches the target structure. Preferably, the customized implant is manufactured by means of rapid prototyping. One kind of rapid prototyping involves forming a standard titanium mesh which resembles a structure to be reconstructed. Another one involves reconstruction of complete bone parts or structures out of artificial material by rapid prototyping techniques. These kinds of techniques are known in the art and allow the construction of structures out of an artificial 3D model by using different materials, like plastic resin or metal powder.

In yet another embodiment, selecting the implant means selecting an implant having a flexible mesh for modelling the implant during surgery. It is to be noted that this process only involves a manipulation of the implant and no surgical intervention with the patient.

In one implementation, the shape dataset is generated by measuring the implant. In this implementation, the exact shape of the implant is known, such that the result of automatic implant positioning resembles the result of reconstruction to a high level of accuracy. Measuring the implant is particularly useful if the implant is generated by rapid prototyping, if the implant comprises a flexible mesh or if the implant is a customised implant. However, measuring the actual implant is also advantageous if the implant is chosen from a database, due to possible variations in the manufacturing process. As an alternative to measuring, the shape dataset can be imported, in particular if a suitable dataset is provided by the manufacturer of the implant.

In one embodiment, automatic implant positioning involves iteratively changing the implant position, determining the difference between the target structure and the implant in its current position, and selecting the position which exhibits the smallest difference. This difference is a measure of the mismatch between the target structure and the implant in its current position. This measure can for example be a least squares measure of the distances between the surfaces—in particular, a defined number of surface points—of the implant and the target structure. Optionally, the measure also takes into account the distance between the surface of the implant and the surfaces of the surrounding objects. An approach based on the surfaces is also called surface matching. The measure can also be the quantitative difference between the volumes of the implant and the target structure. Any other suitable measure can also be used.

The position which results in the smallest difference is selected as the optimum implant position. This minimum difference can be different for different implants. In one implementation, the implant is considered to be suitable if the difference is below a predetermined threshold. One approach is to try different implants until one is found which results in a difference which is below the threshold. Another approach is to try some or all of the available implants and choose the implant which results in the smallest difference.

It is possible to utilise user input data in one or more steps of the method. When determining the target structure, it is possible to utilise input data provided by the user in response to being presented with multiple possible replacements. When selecting an implant, it is possible to utilise user input data such as data which represent the type of implant, i.e. which specify whether the implant is to be obtained from a database, customised or produced using rapid prototyping. When automatically positioning the implant or assessing the suitability of the implant, it is possible to utilise input data provided by the user in response to being presented with an implant position, in particular the optimum implant position, preferably in relation to the structure dataset.

The method in accordance with the invention is in particular a data processing method. The data processing method is preferably performed using technical means, in particular a computer. The computer in particular comprises a processor and a memory in order to process the data, in particular electronically. All the steps described here are in particular performed by a computer. Determining or calculating steps are in particular steps of determining data within the framework of the technical data processing method, in particular within the framework of a program. A computer is in particular any kind of data processing device. A computer can be a device which is generally thought of as such, for example desktop PCs or notebooks or netbooks, etc., but can also be any programmable apparatus, such as a mobile phone or an embedded processor. In particular, a computer can comprise a system (network) of "sub-computers", wherein each sub-computer represents a computer in its own right. A computer in particular comprises interfaces in order to receive data and/or to perform an analogue-to-digital conversion. The data are in particular data which represent physical properties and/or are generated from technical signals. The technical signals are in particular generated by means of technical detection devices and/or analytical devices.

The present invention also relates to a program which, when running on a computer or when loaded onto a computer, causes the computer to perform the method as described above and/or to a program storage medium on which the program is stored (in particular in a non-transitory form) and/or to a signal wave, in particular a digital signal wave, carrying information which represents the program, in particular the aforementioned program. The program in particular comprises code means which are adapted to perform all the steps of the method.

The invention also relates to an apparatus comprising a computer on which said program is running or into the memory of which said program is loaded.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

It is within the scope of the present invention to combine one or more or all of the features of two or more embodiments to form a new embodiment. It is also within the scope of the present invention to omit one or more features of an embodiment as long as the omitted feature(s) is/are not essential to the inventive idea.

The present invention shall now be described in more detail by referring to the accompanying drawings.

Figure 2:
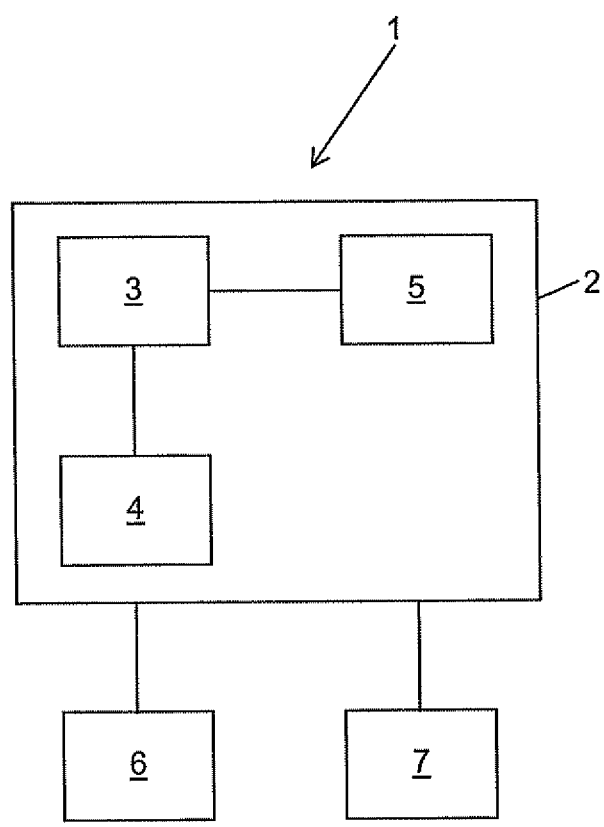

The drawings show:

FIG. 1 a workflow of a method for preparing the reconstruction of a damaged bone structure; and FIG. 2 a schematic representation of an apparatus for executing the workflow of FIG. 1.

The workflow shown in FIG. 1 is based on the assumption that a structure dataset which represents a damaged bone structure to be reconstructed is provided. Preferably, the structure data are three-dimensional image data which depict the damaged structure. In the workflow shown in FIG. 1, the expression "reconstruction template" is used synonymously with the expression "target structure".

Where data are "provided", this means that they are ready for use by the method or program in accordance with the invention. The data can achieve this state of being "ready for use" by for example being generated, in particular detected or captured (for example by analysis apparatus), or by being inputted (for example via interfaces). The data can also achieve the state of being provided by being stored in a data storage medium (for example a ROM, RAM, CD and/or hard drive) and thus ready for use within the framework of the method or program in accordance with the invention. The expression "providing data" encompasses (within the framework of a data processing method) in particular the scenario in which the data are determined by the data processing method or program. The meaning of "providing data" in particular also encompasses the scenario in which the data are received by the data processing method or program, in particular for further processing by the data processing method or program. Thus, "providing data" can also for example mean waiting to receive data and/or receiving the data. The received data can for example be inputted via the interface. "Providing data" can also mean that the data processing method or program performs steps in order to (actively) acquire the data from a data source, for instance a data storage medium (such as for instance a ROM, RAM, database, hard disc, etc.) or via the interface (for instance, from another computer or a network). Preferably, the structure dataset is provided using the DICOM standard.

In step S01, the structure dataset is segmented using atlas segmentation. The atlas represents the undamaged bone structure. In a first alternative, classification data represented by a classification dataset is provided to the segmentation process. This classification data indicates which objects in the atlas correspond to defective or healthy objects in the structure dataset. This classification dataset might be provided by an operator such as a surgeon. The atlas is first matched to the structure dataset, wherein objects in the atlas indicated as being defective could be ignored in the matching process. From the matched atlas, the structure dataset is then segmented into objects and objects indicated as defective in the atlas are also classified as defective in the segmented structure dataset. In a modification of this alternative, the classification data indicates objects of interest which are to be identified and segmented in the structure dataset. Objects of interest could be mirrored counterparts of defective objects in the structure dataset and/or at least one object surrounding a defective object. The objects of interest can be marked in the atlas or in a list of objects in the atlas. With this approach, the time needed for matching and segmenting is minimised, because objects in the atlas apart from the objects of interest are disregarded in the segmentation process.

In a second alternative, the whole atlas is matched to the structure dataset during atlas segmentation. Defective and healthy objects are then classified in the matched atlas, either automatically or by an operator such as a surgeon who marks the objects in the segmented structure dataset, in the matched atlas or in a list of objects in the atlas.

In step S02, the target structure is determined. The target structure is the structure to be achieved by the reconstruction. Preferably, the target structure includes the whole bone structure. Alternatively, the target structure corresponds to the damaged objects within the bone structure only.

FIG. 1 depicts several approaches for determining the target structure. One approach is to mirror healthy objects within the bone structure in order to fill the gaps caused by the defective objects. Instead of a healthy object within the bone structure, an object of the matched atlas which is symmetrical to the defective object can be mirrored. This object in the matched atlas is considered to fairly accurately represent the corresponding healthy object in the bone structure. The mirrored version of this object can then be considered as fairly accurately representing the desired shape of the defective object.

A second approach is to select a reconstruction template from the atlas which was used to segment the structure dataset. Since the atlas is matched to the structure dataset, the objects in the atlas corresponding to the defective objects within the bone structure are considered to fairly accurately represent the defective objects in their undamaged condition.

A third approach is to select a reconstruction template from a database or to receive it as a 3D import. The database can comprise templates which are generated by analysing the bone structures of reference subjects. The database can also comprise templates corresponding to readily available implants. Using a 3D import, a specially designed shape can be used as the target structure.

In a fourth approach, fragments of fractured objects are re-arranged so as to derive the original shape of the defective objects, which can then be used as the target structure.

In a fifth approach, a reconstruction template is built or selected from 2D information. The reconstruction template is for example built from photographs of the patient which were taken before the bone structure was damaged.

Once the target structure has been determined, a suitable implant has to be found in order to emulate the desired target structure. In step S03, a determination is first made as to whether or not an implant database is to be used. If an implant database is to be used, the workflow continues to step S04. In step S04, an implant is selected from the database. This database for example comprises readily available implants provided by a supplier and the respective shapes of the implants.

In step S05, the selected implant is automatically positioned. In this step, the optimum position of the selected implant is determined based on the shape of the implant, in particular without making any statement about the suitability of the implant. As an option, automatic implant positioning can be partly or fully replaced by virtual manual implant positioning during which an operator such as a surgeon virtually positions the implant, for example using a computer which provides appropriate input and display means. The operator sets a virtual position of the implant within the structure dataset. The manually set position can be used in the subsequent method step or can be used as a starting position for automatic implant positioning.

In step S06, a check is made as to whether or not the implant is suitable. If this is the case, the implant data are exported for navigation in step S07. If it is determined in step S06 that the implant is not suitable, the workflow continues to step S08 in which a check is made as to whether or not the currently selected implant is an implant generated by rapid prototyping or a customised implant. If this is the case, the workflow returns to step S04 and resumes searching for an implant in the database.

If the implant is not a customized implant, i.e. the implant was taken from the database, then a check is made in step S09 as to whether there are any more implants in the database, i.e.

whether the database contains other implants which have not yet been checked for suitability. If there are other implants in the database, the next implant is selected from the database in step S10 and the workflow continues at step S05 by positioning the next implant and checking its suitability.

If there are no more implants in the database, a customized implant is manufactured in step S11. This includes exporting the target structure or a part of the target structure in order to enable a customised implant to be manufactured. In step S12, the shape of the customised implant is acquired. The shape is represented by actual shape data. The actual shape data can be acquired by measuring the customized implant or by importing the shape of the customized implant, for example from data provided by the manufacturer of the customized implant. Acquiring the actual shape is advantageous because it may deviate from the desired shape of the target structure.

Once the actual shape of the customised implant has been acquired, the workflow continues at step S05 by positioning the implant and checking its suitability.

If it is determined in step S03 that an implant database is not to be used, the workflow branches off to step S11, in which the target structure or a part of the target structure is exported in order to enable a customised implant to be manufactured. After the customised implant has been manufactured, its shape is acquired in step S12 as explained above, and the workflow continues at step S05, in which the implant is positioned and checked for suitability.

Several amendments to the workflow outlined above are possible, both individually and in any possible combination. One possible amendment is that if an implant is selected from a database, the automatic implant positioning in step S05 does not rely on the information on the shape of the implant provided by the database. Instead, the actual shape of the implant can be acquired as explained above and used for (automatic) implant positioning.

In another amendment, the workflow does not return from step S08 to step S04 if the implant is a customised implant, but rather to step S03. In this case, the implant database is not automatically used if the customised implant is not suitable.

In yet another amendment, the workflow does not automatically branch off from step S03 to step S11 if an implant database is not to be used. Instead, a determination is made as to whether a customised implant is to be used. This would mean an additional decision step between steps S03 and S11, with the workflow either branching off to step S11 or ending, depending on the decision. A similar determination may be made between steps S09 and S11.

In yet another amendment, at least one exit is provided in order to quit the workflow at a suitable stage. One such suitable exit would be between steps S03 and S11, particularly if a customised implant has already been checked for suitability. In particular, a determination can be made whether or not a customized implant has already been tested. If this is the case, the workflow ends. If this is not the case, a customized implant is generated or a determination is made whether or not a customized implant is to be used. Another possible position for an exit would be after step S11, in particular if the customized implant is considered as correctly representing the target structure. Yet another possible position for an exit would be between steps S09 and S11, such that a customised implant is not used if a suitable implant is not found in the database.

FIG. 2 schematically shows an apparatus 1 for processing the workflow of FIG. 1. The apparatus 1 comprises a computer 2 which is connected to an input device 6 and a display device 7. The computer 2 contains a central processing unit 3, a memory 4 and an interface 5. The memory 4 stores program data and application data, such as the structure dataset and the shape dataset. The memory 4 can also encompass the working memory of the computer 2. In general, the memory 4 comprises at least one of a hard disc drive, an optical drive, a flash memory, a RAM, a ROM or any other suitable memory or data storage medium.

The interface 5 is at least used for receiving data such as the structure data set and/or the shape dataset. The interface can in particular be used to connect the computer 2 to a device which provides data to the computer 2. This device can be a storage medium or a device which generates the data, such as a CT or x-ray device. The interface 5 can also be used to connect the computer 2 to a device for measuring the shape of an implant. This device could be a CT or x-ray device, such as the one used to determine the structure data set, or any other suitable device such as for example a 3D laser scanner.

The input device 6 can comprise at least one of a keyboard, a touchpad, a mouse, a trackball, a pointer or any other suitable device for inputting information into the computer 2. The display device 7 can for example be a monitor or any other suitable display for providing information to a user. The display device 7 can for example be used to display the damaged bone structure with the defective objects replaced by the selected implant, preferably at its optimum position. Instead of or in addition to a visual display device, other devices for outputting information, such as acoustic or tactile information, can also be used.

An adaptor can be used to assemble multiple parts of the apparatus 1 or to attach the apparatus 1 to another device. Such an adaptor is also part of the present invention. An adaptor for fixing a (medical) apparatus to one or two support structures is characterised in that the adaptor is constructed in three parts from a bearing part and two support parts, wherein the bearing part can be connected to the medical apparatus, the first support part can be connected to a first support structure, and the second support part can be connected to a second support structure, and wherein the adaptor can assume at least three states: a first state, in which the bearing part is connected, free of clearance, to the first support part only; a second state, in which the bearing part is connected, free of clearance, to the second support part only; and a third state, in which the bearing part is connected, free of clearance, to the first support part and the second support part.

The invention claimed is:

1. A method, carried out by a computer, for preparing the reconstruction of a damaged bone structure using an implant, comprising:
   a) performing atlas segmentation on a structure dataset which represents a structure to be reconstructed, and determining one or more healthy objects and one or more defective objects within the damaged bone structure;
   b) determining a target structure by modelling replacements for the one or more defective objects within the damaged bone structure;
   c) selecting an implant on the basis of the target structure, and providing a shape dataset which represents the shape of the implant;
   d) positioning the selected implant in order to find an optimum implant position;
   e) determining whether or not the selected implant is a suitable implant, and returning to step c) if the selected implant is determined to not be a suitable implant; and
   f) exporting the suitable implant to a medical navigation process.

2. The method of claim 1, wherein the replacements are modelled in step b) by mirroring the one or more healthy objects within the damaged bone structure or a corresponding structure.

3. The method of claim 1, wherein the replacements are modelled in step b) by selecting at least parts of the atlas as the target structure.

4. The method of claim 1, wherein the replacements are modelled in step b) by selecting a template from a database or selecting an imported 3D template as the target structure.

5. The method of claim 1, wherein the replacements are modelled in step b) by rearranging fragments of the damaged bone structure in order to reconstruct the target structure.

6. The method of claim 1, wherein the replacements are modelled in step b) by building a target structure from 2D information.

7. The method of claim 1, wherein step c) comprises selecting an implant from a database.

8. The method of claim 1, wherein step c) comprises selecting an implant which is generated by rapid prototyping.

9. The method of claim 1, wherein step c) comprises selecting an implant which is generated as a customised implant.

10. The method of claim 9, further comprising exporting the target structure to a manufacturing process for the customised implant.

11. The method of claim 1, wherein step c) comprises selecting an implant having a flexible mesh for modelling the implant during surgery.

12. The method of claim 1, further comprising automatic implant positioning by iteratively changing the implant position, determining the difference between the target structure and the implant in its current position, and selecting the position which exhibits the smallest difference.

13. The method of claim 1, wherein the automatic implant positioning comprises surface matching.

14. A non-transitory computer-readable storage medium on which a program is stored, which, when running on a computer or when loaded onto a computer, causes the computer to perform a method for preparing the reconstruction of a damaged bone structure using an implant, comprising:
   a) performing atlas segmentation on a structure dataset which represents a structure to be reconstructed, and determining one or more healthy objects and one or more defective objects within the damaged bone structure;
   b) determining a target structure by modelling replacements for the one or more defective objects within the damaged bone structure;
   c) selecting an implant on the basis of the target structure, and providing a shape dataset which represents the shape of the implant;
   d) positioning the selected implant in order to find an optimum implant position;
   e) determining whether or not the selected implant is a suitable implant, and returning to step c) if the selected implant is determined to not be a suitable implant; and
   f) exporting the suitable implant to a medical navigation process.

15. A computer comprising the non-transitory computer-readable storage medium of claim 14.

* * * * *